United States Patent [19]

Dixon et al.

[11] 4,236,036

[45] Nov. 25, 1980

[54] CATALYTIC ALKYLATION OF HYDROCARBONS

[75] Inventors: Rolland E. Dixon; Charles C. Chapman, both of Bartlesville, Okla.

[73] Assignee: Phillips Petroleum Company, Bartlesville, Okla.

[21] Appl. No.: 27,424

[22] Filed: Apr. 5, 1979

[51] Int. Cl.³ .............................................. C07C 2/58
[52] U.S. Cl. ................... 585/331; 585/332; 585/719; 585/723; 585/724; 422/111
[58] Field of Search ............... 585/331, 332, 723, 724, 585/719

[56] References Cited

U.S. PATENT DOCUMENTS

| | | | |
|---|---|---|---|
| 2,373,101 | 4/1945 | Clarke | 585/331 |
| 2,382,899 | 8/1945 | Newman | 585/723 |
| 2,387,162 | 10/1945 | Matuszak | 585/331 |
| 2,399,368 | 4/1946 | Matuszak | 585/331 |
| 3,408,419 | 10/1968 | Herber et al. | 585/724 |
| 3,825,617 | 7/1974 | Hervert | 585/723 |
| 3,845,158 | 10/1974 | Sobel | 585/331 |
| 3,953,538 | 4/1976 | Boney | 585/332 |

*Primary Examiner*—C. Davis

[57] ABSTRACT

A continuous process for alkylating an alkylatable hydrocarbon with an alkylating agent in the presence of an acid-type catalyst in which the alkylatable hydrocarbon is contacted with the alkylating agent in the presence of the catalyst at a temperature and for a time sufficient to alkylate the alkylatable hydrocarbon, the reaction product is separated into an alkylate product phase and a catalyst phase, containing catalyst-soluble oil, the catalyst phase is cooled to maintain a preselected temperature in the exothermic alkylation zone, the cooled catalyst phase is recycled to the alkylation reaction and a predetermined concentration of catalyst-soluble oil is maintained in the catalyst phase by at least periodically heating an alkylating agent to a temperature above the reaction temperature, contacting the heated alkylating agent with one of the separated recycle catalyst, separated rerun catalyst, fresh catalyst or mixture thereof and combining the resultant reaction product with separated recycle catalyst prior to the cooling of the separated recycle catalyst phase. A start-up procedure, in which the content of catalyst-soluble oil in the catalyst phase is brought up to the predetermined concentration, is also disclosed in which the reaction product of the heated alkylating agent and the catalyst is added to the catalyst phase. Apparatus for carrying out the above processes is also described.

25 Claims, 3 Drawing Figures

CATALYTIC ALKYLATION OF HYDROCARBONS

BACKGROUND OF THE INVENTION

The present invention relates to a catalytic alkylation process and apparatus. In a more specific aspect, the present invention relates to a catalytic alkylation process in which an alkylatable hydrocarbon is contacted with an alkylating agent in the presence of an acid-type catalyst and the catalyst is cyclically circulated through the system. In yet another aspect, the present invention relates to a catalytic alkylation process and apparatus in which an acid-type catalyst is cyclically circulated through the system to produce an alkylate product of improved octane number.

Numerous processes are known in the prior art for alkylating an alkylatable hydrocarbon with an alkylating agent in the presence of a catalyst. From a commercial standpoint, the most prevalent systems involve the cyclic circulation of an acid-type catalyst, such as hydrofluoric acid, sulfuric acid, etc. through a reaction zone, a separation zone, a cooling zone and back to the reaction zone.

One such process for the alkylation of hydrocarbons, utilizing the cyclic circulation of the catalyst, introduces the reactant hydrocarbons in a gaseous phase. In this system the gaseous hydrocarbon feed mixture is introduced at a high velocity to the lower portion of the reaction zone and into a continuous catalyst phase maintained in the reaction zone. Suitable conditions of temperature and residence time are provided in the reaction zone whereby the alkylatable hydrocarbon is alkylated. A stream comprising catalyst, alkylate product and unconsumed reactants passes from the upper portion of the reaction zone into a settling zone, wherein separation occurs between the alkylate product phase and the catalyst phase. The alkylate product phase is withdrawn from the settling zone for further processing, as by fractionation, and the catalyst phase is passed downwardly to a cooling zone and thence back into the reaction zone.

Another process, based on the cyclic circulation of the catalyst, which overcomes certain of the inherent deficiencies of the gas phase process and permits operation at low reaction temperatures, introduces the reactant hydrocarbons in the liquid phase. In this process, the hydrocarbon reactants are introduced into the bottom of the reaction zone through constricted passageways, thereby creating a liquid lift system, whose motive power comes from the difference in density of the flowing streams and to some extent from the kinetic energy of the inlet hydrocarbon stream, and at the same time creating small droplets of reactants having a high interfacial area which result in a desirably high reaction rate. The reactant hydrocarbons and catalyst move upwardly through an elongated, tube-type reaction zone, the effluent, including alkylate product, catalyst and unreacted hydrocarbons, is discharged from the reaction zone into a horizontally-disposed settler-surge vessel, an alkylate product phase is withdrawn for further processing and a catalyst phase is passed downwardly through a tube-type conduit to a horizontally-disposed cooler and thence back into the reaction zone.

It has generally been recognized in the art that in order to obtain an alkylate product of maximum octane number, the weight percent total acidity of the catalyst should not exceed a given amount. While the tolerable acidity of the catalyst will vary depending upon the reactant hydrocarbons and the temperature of operation, it is generally thought that the total acidity of the catalyst under any conditions should not be higher than about 90 percent, that alkylate products of highest octane number are obtained at acidities substantially lower than this and, consequently, that the weight percent total acidity of the catalyst for optimum octane number should be between about 87 percent and 67 percent. Consequently, the catalyst is in some way diluted so as to maintain the desired total acidity. Obviously, water would be the logical diluting agent to utilize. However, the presence of excessive amounts of water, in systems utilizing acid catalysts, creates problems in that, in conjunction with the acid, water is highly corrosive to the alkylation system and catalyst handling system. Therefore, the acid catalyst is normally utilized in an essentially anhydrous condition. There is a tendency in alkylation systems for water to accumulate as the result of its presence in the hydrocarbon reactants and its absorption from the atmosphere. Therefore, alkylation systems employing acid-type catalysts normally include a so-called catalyst "rerun" system through which catalyst is at least periodically passed in order to remove water therefrom. The rerun system will normally involve withdrawing a portion of the catalyst phase as it flows from the separator to the cooler. The withdrawn catalyst phase is heated to a temperature sufficient to vaporize residual alkylate, unreacted hydrocarbons, and the major part of the acid phase from the water. Water is withdrawn as a bottoms product from the rerun separator while the vapor phase is recycled to the settler-surge zone or back to the separated acid phase. Generally, a portion of the alkylatable hydrocarbon, in liquid form, is utilized as a reflux and another portion, in gaseous form, as a stripping medium in the rerun separator.

It is also recognized in the art that a certain amount of dilution of the catalyst phase occurs in the reaction zone itself. Specifically, what is known as a catalyst- or acid-soluble oil (ASO) is produced in the reaction zone, which inherently acts as a diluent for the catalyst phase. While the specific nature of the acid-soluble oil has not been completely established, it is generally accepted that it comprises predominantly polymeric materials with minor amounts of complexes and small or trace amounts of impurities, such as sulfur, to the extent such impurities exist in the alkylation feed materials. These catalyst-soluble oils are retained in the catalyst phase during the separation of the alkylate phase from the catalyst phase and consequently are recycled to the alkylation system. It has also been universally accepted, by those skilled in the art, that the production of catalyst-soluble oil is substantially in excess of that necessary or desirable for dilution of the catalyst. Consequently, the prior art contains suggestions for the removal of the excess catalyst-soluble oil.

Finally, those skilled in the art have recognized the fact that under normal operating conditions the production of catalyst-soluble oils is extremely slow. Accordingly, the prior art has suggested various start-up procedures which will rapidly produce the desirable inventory of catalyst-soluble oil, thereby substantially shortening the time necessary to arrive at full-scale production of alkylate product.

In contrast to the teachings of the prior art, it has now been found that the amount of catalyst diluent which will produce an alkylate product of maximum octane number is within a relatively narrow range below the amounts heretofore suggested by the prior art. Further, it has been found that a very small change in the amount of catalyst diluent, within the narrow range referred to above, has a substantial effect on the octane number of the alkylate product. Also contrary to the teachings of the prior art, it has been found that not all hydrocarbon reactants produce catalyst-soluble oil at the same rate or in the same ultimate volumes. Specifically, it has been found that when reacting an alkylatable hydrocarbon, such as isobutane, with a $C_4$ olefinic hydrocarbon, such as isobutylene, butene-1 and/or butene-2's, catalyst-soluble oils are produced at an extremely slow rate and in relatively small amounts, as compared with other reaction systems. In addition, as the alkylation reaction proceeds, there is a certain attrition of the amount of catalyst-soluble oils in the catalyst phase. While the reasons for this attrition are not fully known, it is believed that a certain amount of the catalyst-soluble oil is carried over with the alkylate product during separation, a greater portion is removed from the system along with water when the catalyst is rerun to remove water and small amounts may actually be consumed during the alkylation reaction. More specifically, it has been found that when an isoparaffin, such as isobutane, is reacted with a $C_4$ olefinic hydrocarbon, such as isobutylene, butene-1, and/or butene-2's, an inordinately long period of time is necessary for starting up the alkylation system and there is normally a net loss of catalyst-soluble oil during the course of the reaction.

It would therefore be highly desirable to provide means for substantially shortening the necessary start-up period and for thereafter maintaining a predetermined amount of catalyst-soluble oil in the catalyst system.

It is therefore an object of the present invention to provide an improved system for the alkylation of hydrocarbons. Another and further object of the present invention is to provide an improved system for the alkylation of hydrocarbons, utilizing a cyclic flow of an acid-type catalyst. A further object of the present invention is to provide an improved system for the alkylation of hydrocarbons, utilizing a cyclic flow of an acid-type catalyst, in which an alkylate product of improved octane number is obtained. Yet another object of the present invention is to provide an improved system for the alkylation of hydrocarbons, utilizing a cyclic flow of an acid-type catalyst, in which the acid-soluble oil content of the catalyst phase is maintained within a predetermined critical range. Another and further object of the present invention is to provide an improved system for the start-up of a system for the alkylation of hydrocarbons, utilizing cyclic flow of an acid-type catalyst. These and other objects and advantages of the present invention will be apparent from the following detailed description of the invention.

SUMMARY OF THE INVENTION

In accordance with the present invention, an improved start-up of a system for the reaction of an alkylatable hydrocarbon with an alkylating agent, employing a cyclically flowing, acid-type catalyst, is provided, involving; conventionally lining out the system to establish a continuous flow of catalyst, and optionally one or both reactants, thereafter, heating an alkylating agent to a temperature above the alkylation reaction temperature, contacting the heated alkylating agent with one of the separated recycle catalyst phases, the separated rerun catalyst, fresh catalyst or a mixture thereof and combining reaction product of the heated alkylating agent and the catalyst with the separated recycle acid phase to produce acid-soluble oils, prior to cooling of the acid phase and subsequent recycling of the acid phase to the alkylation reaction. Once a predetermined concentration of acid-soluble oil has been established in the circulating acid phase, such predetermined concentration of acid-soluble oil is maintained by at least periodically heating further amounts of the alkylating agent to a temperature substantially above the alkylation reaction temperature and adding the heated alkylating agent to the separated acid phase, prior to cooling the separated acid phase and recycling the same to the alkylation reactor.

Inasmuch as there is some confusion of terminology in the art as to which of the reactants is the alkylatable hydrocarbon and which is the alkylating agent, the isoparaffin hydrocarbon, when referred to herein, will be referred to as the "alkylatable hydrocarbon" while the olefinic hydrocarbon will be referred to herein as the "alkylating agent".

DETAILED DESCRIPTION OF THE INVENTION

Figure 1:
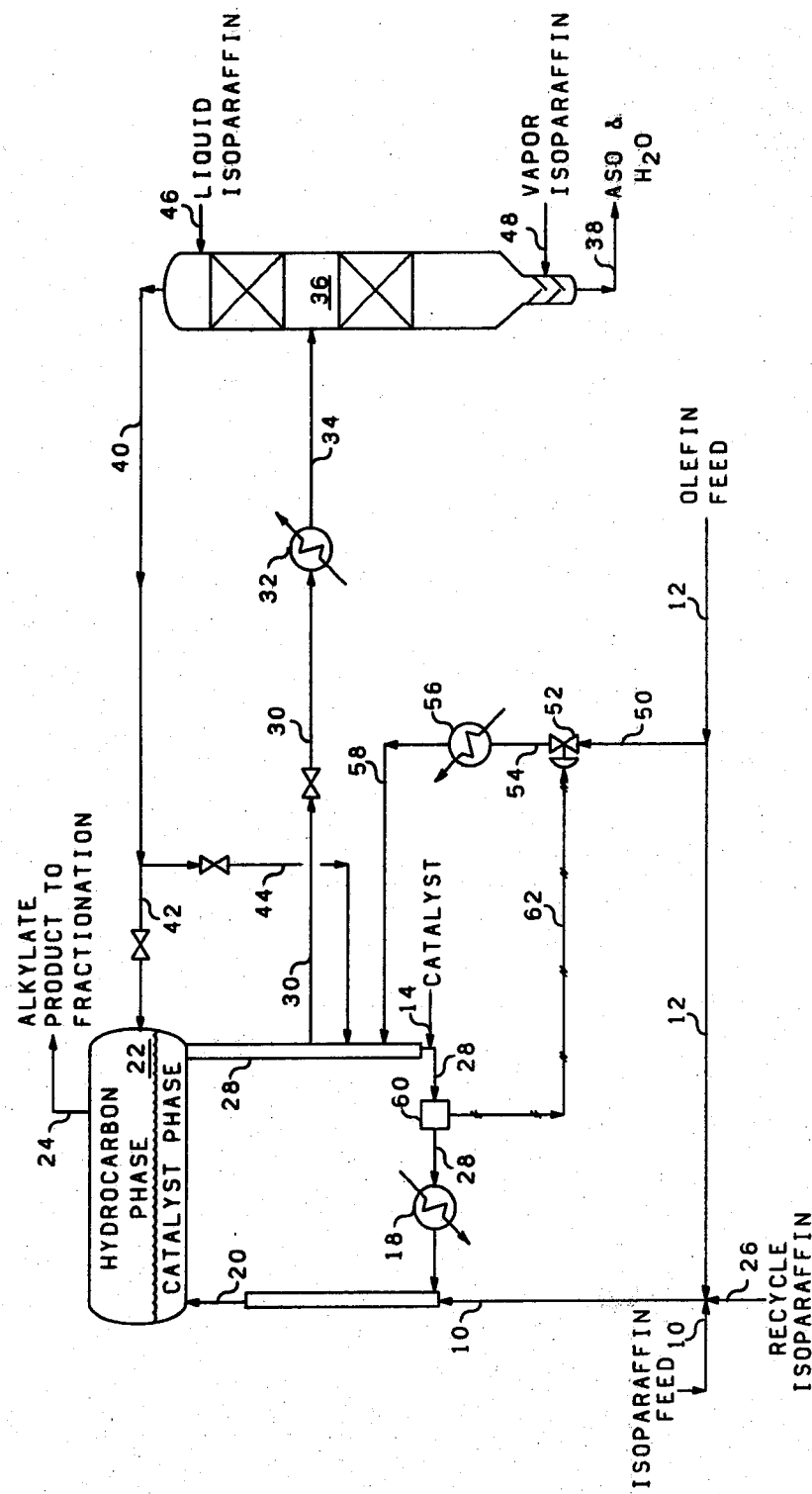
FIG. 1 is a simplified flow diagram of an alkylation system in accordance with one embodiment of the present invention.

While, as previously indicated, the present invention can be carried out in any type of reactor system utilizing a cyclically flowing, acid-type catalyst, the preferred system in accordance with the present invention is a cyclic catalyst system in which the mixture of hydrocarbon feed materials is maintained in a liquid state. Such a system using HF catalyst is described in detail in U.S. Pat. No. 3,213,157, which is incorporated herein by reference. Briefly, the system comprises a vertically-disposed tubular reactor into which a mixture of the hydrocarbon feed materials and the catalyst is introduced adjacent to the bottom of the reactor, a horizontally-disposed settler-surge vessel, adapted to receive effluent from the top of the reactor and separate the effluent into an alkylate product phase, which is further processed by fractionation or the like, and a catalyst phase, a vertically-disposed tubular catalyst return conduit wherein the catalyst phase passes downwardly, and an essentially horizontally-disposed acid phase cooler, which is cooled by water. This entire system is in open communication throughout for cyclic catalyst flow. Normally, acid phase is at least periodically withdrawn as a side stream from the separated acid phase conduit and passed to a heater where it is heated to a temperature sufficient to cause separation of a liquid phase, comprising predominantly water and some acid-soluble material, and a vapor phase comprising predominantly catalyst, unreacted feed materials and some alkylate. The heated acid phase is then passed to a rerun separator, which is normally operated with a liquid portion of the alkylating agent, as a reflux, and a vapor portion, as a stripping agent. The vapor phase product of the rerun separator is then returned to the systems settler-surge vessel or back to the catalyst phase at a point below the point at which catalyst phase was withdrawn for rerun, while the water and any acid-soluble material present is withdrawn as a liquid phase and discarded.

Conventionally, the alkylation reaction can comprise the reaction of an isoparaffin with an olefin or other alkylating agent, reaction of a normal paraffin with an olefin or other alkylating agent or the reaction of an aromatic hydrocarbon with an olefin or other alkylating agent. However, as previously indicated, it has been found that the reaction of an isoparaffin with a $C_4$ olefin, such as isobutylene, butene-1, and/or butene-2's, is peculiar and therefore a preferred embodiment of present invention is directed to a reaction involving these specified materials and mixtures thereof. One preferred mixture is an isoparaffin and a typical mixed "butenes" product from a catalytic cracking operation, which will comprise about 25.0% by volume of butene-1, about 30.0% by volume of isobutylene and about 45.0% by volume of butene-2's.

A variety of alkylation catalysts can be employed in the alkylation reaction, including well known acid catalysts such as sulfuric acid, hydrofluoric acid, phosphoric acid; metal halides, such as aluminum chloride, aluminum bromide, etc.; and other alkylation catalysts. A preferred catalyst for use in the present invention is hydrofluoric acid.

The reaction may be carried out at pressures varying from atmospheric to as high as 1000 psi and higher, preferably about 125 to 220 psia, and at residence times of 20 seconds to 5 minutes. The pressure is preferably sufficient to maintain the hydrocarbon reactants in their liquid phase.

In an alkylation reaction, involving the alkylation of isoparaffins with olefins, a substantial molar excess of isoparaffin to olefin is employed to provide a feed ratio in excess of 1/1, usually about 4/1 to about 70/1 and preferably about 5/1 to about 20/1.

As previously indicated, the reaction zone is preferably maintained under sufficient pressure to insure that the hydrocarbon reactants and the alkylation catalyst are in a liquid phase. The temperature of the reaction will vary with the reactants and with the catalyst employed but generally ranges from between about $-40°$ F. to about 150° F. However, in the reaction of an isoparaffin, such as isobutane, with a $C_4$ olefin, such as butylenes, butene-1 and/or butene-2, the reaction temperature is preferably between about 60° and about 100° F. and, ideally, about 90° F.

Conventionally, the system is lined out by first introducing a dried isoparaffinic hydrocarbon to the unit and passing it continuously through the alkylation reactor, the settler, and the isoparaffin stripper and then recycling the same to the alkylation reactor in order to dry out the alkylation apparatus before fresh, essentially anhydrous hydrofluoric acid is introduced. Generally, drying of the feed is accomplished by passing the isoparaffin through molecular sieve dryers or other drying means well known in the art. The dried isoparaffin is then continuously charged to the unit until a rate of continuous recycle equal to the rate of recycle during normal operation is attained. After it has been determined that the alkylation apparatus is sufficiently dry and the isoparaffin recycle rate has been established, hydrofluoric acid is charged to the alkylation apparatus and continuously circulated through the reactor, the settler, the cooler and back to the reactor. This circulation continues until the desired normal circulation rate of hydrofluoric acid is attained. Thereafter, the olefinic feed material is mixed with the isoparaffinic feed material and introduced into the reactor and continuous operation is commenced.

Referring now to FIG. 1 of the drawings, the isoparaffinic feed is introduced through line 10, the olefinic feed through line 12 and the catalyst through line 14. Initially when the system is being lined out, only isoparaffinic feed is passed through line 10 to the bottom of reactor 16. However, during normal operation, the olefin feed and the isoparaffin feed are introduced, as a mixture or individually, at one end of the catalyst cooler 18. During start-up, circulation of the isoparaffin feed through the system, as previously described, catalyst is introduced through line 14 and recycled through line 28 to cooler 18 and back to reactor 16. In a preferred system, the cooler 18 is a horizontally-disposed, elongated cooler and the acid catalyst is introduced at a point along the length of the cooler, displaced from the point of introduction of the hydrocarbon feed materials. When the system is lined out in accordance with conventional practice and the introduction of olefin feed is begun, the reactors, coolers, etc. contain an inventory of catalyst, such that the level of catalyst extends into the settler-surge vessel 22. Therefore, the catalyst present in the alkylation system substantially exceeds in quantity the amount of hydrocarbon feed and hence constitutes a continuous phase in the system.

Effluent from reactor 16 are discharged through line 20 to settler-surge vessel 22. In settler-surge vessel 22, the effluent is separated into an alkylate product phase, which is discharged through line 24. The alkylate product phase is passed through line 24 to an isoparaffin stripper (not shown), wherein isoparaffin is removed from the reaction products and recycled to the system through line 26. The remainder of the alkylate product is then further processed in accordance with conventional practice. In the settler-surge vessel 22, an acid phase or catalyst phase is separated and passed downwardly through line 28. The acid phase passes through cooler 18 and back to reactor 16. As necessary or desirable, separated acid phase is withdrawn through line 30 and passed to heater 32. The heated acid phase then passes through line 34 to rerun separator 36. In separator 36, the acid phase is separated into a bottoms product, comprising principally water and some catalyst soluble oil, which is discharged through line 38. The overhead fraction from separator 36, comprising acid catalyst, any isoparaffin present in the acid-phase and some alkylate product, along with isoparaffin used as reflux and stripping fluid in rerun column or separator 36, is discharged through line 40. Depending upon the temperature, composition, etc. of the overhead product in line 40, this product may be returned to the system at any one of a variety of points, for example, through line 42 to the settler-surge vessel 22 or through line 44 back to the catalyst phase in line 28. Separator 36 is normally operated by introducing a quantity of liquid isoparaffin, as a reflux, through line 46 and a quantity of vapor phase isoparaffin, as a stripping medium, through line 48.

As previously indicated, it has been found that in the reaction of an isoparaffin, such as isobutane, with a $C_4$ olefin, such as isobutylene, butene-1 and/or butene-2's, an inordinately long period of time is required to build up a sufficient amount of catalyst-soluble oil under normal reaction conditions in reactor 16. Consequently, in accordance with one embodiment of the present invention, after normal flow of isoparaffin and acid or acid base has been established in the system, a portion of the alkylating agent or another alkylating is passed through line 50, through control valve 52 and through line 54 to heater 56. In heater 56, the alkylating agent is heated to a temperature above the alkylation reaction temperature and preferably above the temperature of the separated catalyst phase in line 28, for example between about 160° and about 215° F. and, preferably, a temperature of about 170° F. The heated alkylating agent is then passed through line 58 and added to the recirculating acid phase in the system at some point prior to the cooling of the acid phase in cooler 18. Normally, the acid phase flowing from settler-surge vessel 22 through line 28 will be between about 70° and 115° F. The heated alkylating agent, when combined with the recirculating acid phase in line 28, brings the temperature of the combined materials up to a temperature of about 140° to about 160° F., preferably about 150° F. It has been found that at this temperature the alkylating agent will react with the circulating acid phase to produce substantial amounts of acid-soluble oil at a rapid rate. The resultant acid-soluble oil is believed to be polymeric material averaging about 12 to 40 carbon atoms per molecule. The alkylating agent may be in a vapor or liquid phase when contacted with the circulating acid phase. It is also contemplated that the heated alkylating agent may be started after the introduction of the isoparaffin-olefin mixture is began.

Once the desired quantity of catalyst-soluble oil has been established, part of the system alkylating agent or another alkylating agent is at least periodically passed through heater 56 in amounts sufficient to maintain a predetermined desired quantity of catalyst-soluble oil in the recirculating catalyst. It has been found that such predetermined amount of catalyst-soluble oil is preferably between about 4 and 25 weight percent of the catalyst phase and still more preferably between about 5 and 15. The total acidity of the catalyst is preferably between about 75% and about 90%, the difference between the total of the acid plus acid-soluble oil and 100 percent being water and probably unreacted alkylatable material.

In both the start-up and the normal operation of the alkylation system, it is necessary to maintain close control over the quantity of catalyst-soluble oil in the circulating catalyst. This is true, since it has been found that extremely small variations in the quantity of catalyst-soluble oil result in substantial differences in the octane number of the alkylate product. Therefore, further in accordance with the present invention, the quantity of catalyst-soluble oil is at least periodically determined, both during the start-up of the system and during normal operation of the system, and valve 56 is controlled in accordance with this determination in order to maintain the desired level of catalyst-soluble oil in the system. Specifically, an indicator-controller 60 is mounted at some point in the catalyst recycle line 28 prior to the passage of the recirculating catalyst through cooler 18 and subsequent to the introduction of heated alkylating agent to the catalyst system through line 58. Indicator-controller 60 transmits a signal through line 62 to control valve 52. The control system, consisting of indicator-controller 60, line 62 and valve 52 may take any one of a variety of known forms. The system may be electrical, pneumatic, a combination of these two or a combination of one or both with a mechanical system.

Figure 2:
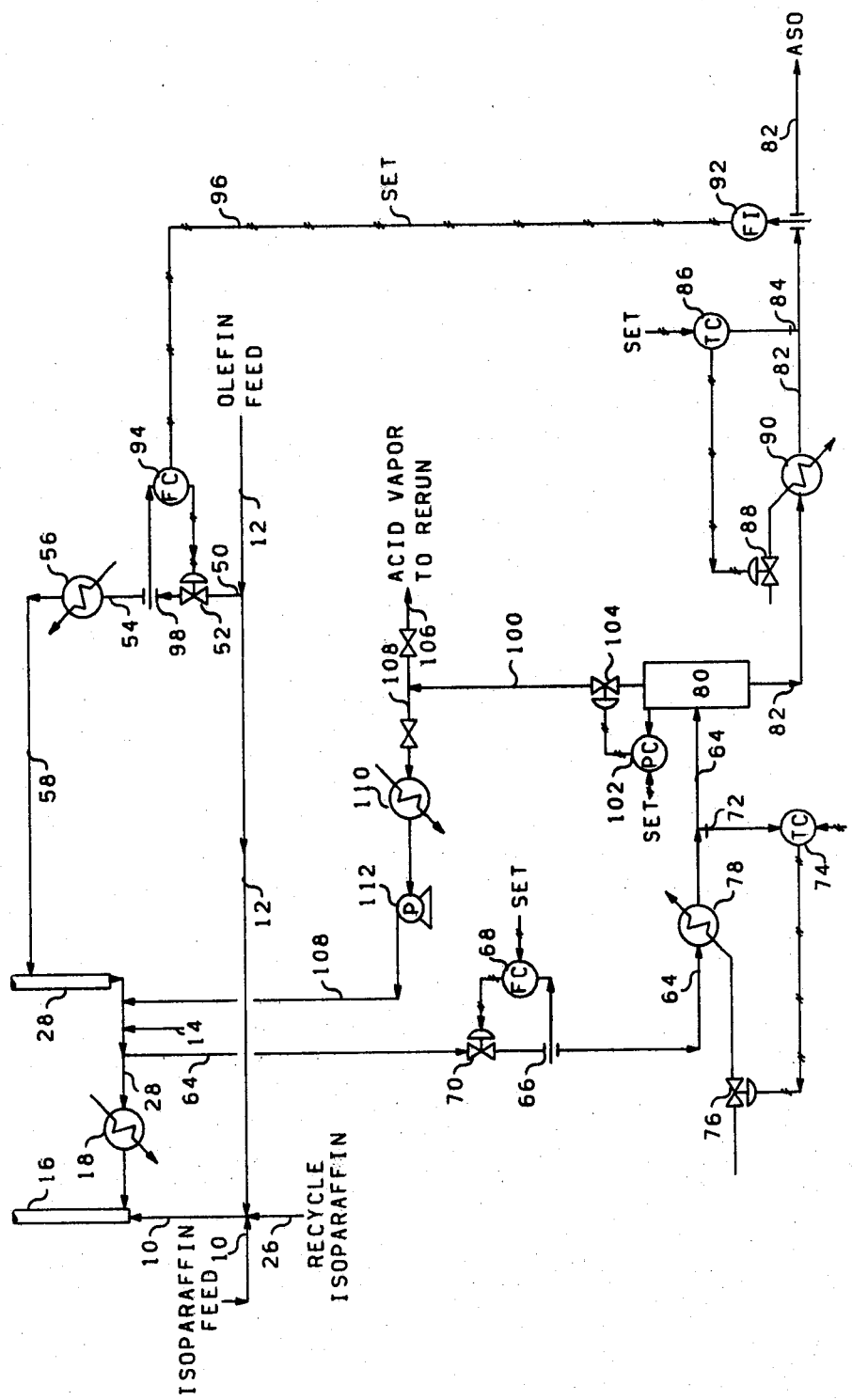
FIG. 2 is a more detailed diagram of a control means for the system of FIG. 1.

FIG. 2 of the drawings shows in somewhat greater detail a specific example of the control system 60-62-52. In accordance with FIG. 2, a small slipstream of separated acid phase is withdrawn from line 28 through line 64. The volume of this slipstream is controlled by flow indicator 66 in combination with flow controller 68 and valve 70. Flow controller 68 is set at a predetermined flow by the operator. The temperature of the withdrawn sample stream, passing through line 64, is also measured by means of indicator 72. The measured temperature is transmitted to temperature controller 74 and a control signal is transmitted to valve 76 which controls the volume of heating medium to heater 78. Temperature controller 74 is set so as to heat the sample of the acid phase in line 64 to a temperature sufficient to remove all acid as a vapor and leave the remaining acid-soluble oil as a liquid bottoms product in separator 80. From separator 80 the unvaporized catalyst-soluble oil is discharged through line 82. Inasmuch as the volume of the catalyst-soluble oil is so small it can be discarded without having any impact on the overall operation. The catalyst-soluble oil line 82 may be temperature controlled by the combination of temperature indicator 84, temperature controller 86 and valve 88 on the coolant line to cooler 90. The volume of catalyst-soluble oil in line 82 is measured by flow indicator 92 which sends a signal or set point to flow controller 94 through line 96. The flow through line 54 is measured by flow indicator 98. The flow measured by indicator 98 is transmitted to flow controller 94 which in turn controls the flow through valve 52. Flow controller 94 may include a ratio controller, and add- or subtract circuit or like means. The separated vapor phase acid is discharged from separator 80 through line 100 and the pressure in separator 80 is regulated by pressure controller 102 and valve 104. Acid from line 100 may be recirculated to the acid rerun system through line 106 or to the acid phase in line 28 through line 108, including, cooler 110 and pump 112 (which can be an eductor powered by isobutane).

Figure 3:
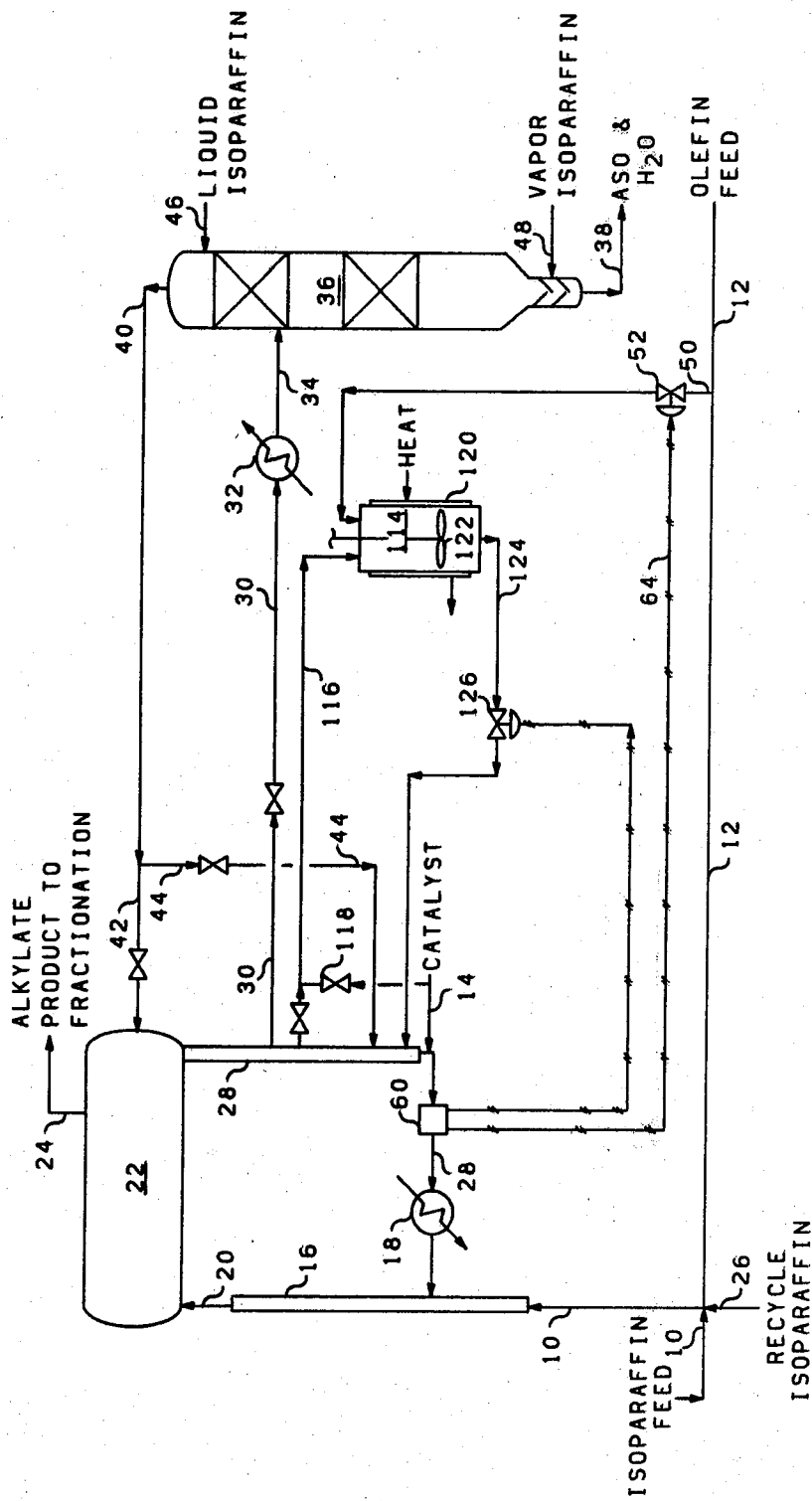
FIG. 3 is a simplified flow diagram of a second embodiment of the present invention.

FIG. 3 illustrates a second embodiment of the present invention in which an acid-soluble oil reactor 114 replaces the heater 56 of FIG. 1. Reactor 114 is supplied with olefin through line 50. At least a portion of the circulating acid-phase may be introduced through line 116 or fresh make-up acid or recycle acid from a fractionator (not shown) from line 14 may be introduced through line 118. Reactor 114 is provided with a heating means 120 to heat the reactants, to a temperature above the alkylation temperature, and a mixer 122. Acid-soluble oil, formed in reactor 114 is added to the circulating acid phase in line 28 through line 124. Flow control valve 126 is mounted in line 124. Alternatively, or in addition to controlling the flow through line 124, flow of olefin through line 50 can be controlled, as previously explained. Otherwise, the alkylation system operates in substantially the same manner as the embodiment of FIG. 1 and the control system operates in the manner described with reference to FIG. 2.

As previously indicated, the alkylating agent utilized to generate acid-soluble oil, in accordance with the present invention, may be a portion of the alkylating agent feed. However, were the alkylating agent is $C_4$ olefins it may be desirable, at least during startup to utilize other olefinic alkylating agents. For example, propylene, amylenes, butadiene, etc. may be utilized, since these materials generate larger proportions of acid soluble oils at a more rapid rate in the order listed. Specifically, propylene generates acid soluble oils in greater quantities than butylene and butadiene in the largest quantities.

The following example illustrates an operation in accordance with the embodiment of FIG. 1.

EXAMPLE I

The following example illustrates operation in accordance with the embodiment of FIG. 1.

Example I

Pilot plan runs showed that when butylenes were used to alkylate isobutane using HF catalyst having 13 weight percent polymer (or produced acid soluble oil) at an HF catalyst to total hydrocarbon volume ratio of about 4 to 1, a total isobutane to olefin mol ratio of 13 to 1 and a residence time of about 60 seconds, the debutanized alkylate had a Research Octane Number (Occ TEL) of 96.5. The reactor pressure was about 160 psig and the reaction temperature was about 90° F.

Pilot plant runs using mixed olefins (propylene and butylenes) at the same ratios of catalyst to total hydrocarbon, total isobutane to olefin, and residence times, but using HF catalyst with only about 3 weight percent acid soluble oil (no added or produced polymer or ASO), the Research Octane Number (Occ TEL) was 93.5 for the debutanized alkylate. The pressure in the reactor was about 160 psig, but the temperature was 40° F. It should be noted here, that it is known that at 40° F. the octane should be higher than at 90° F., all other conditions being the same, approximately a gain of one-half to one octane for each 10° F. lowering of temperature should be realized.

TABLE I

| | |
|---|---|
| Butylenes Feed, B/H, | 100 |
| Composition, Vol. %, | |
| Butene-1 | 25 |
| Isobutylene | 30 |
| Butene-2's | 45 |
| Isobutane Feed, B/H, | 100 |
| Isobutane Recycle, B/H | 1200 |
| HF Catalyst, B/H | 5600 |
| Composition, Wt. % | |
| HF, | 78 |
| H$_2$O, | 0.5 |
| Acid Soluble Oil | 13 |
| Light Hydrocarbons, | 8.5 |
| (Debutanized Alkylate), B/H | 175 |
| Research Octane No. (Occ TEL) | 96.5 |
| Reactor Conditions | |
| Pressure, psig, | 160 |
| Temperature (inlet), °F., | 90 |
| H/FTotal Hydrocarbon Vol. Ratio, | 4:1 |
| Total IC$_4$/Olefin Mol Ratio, | 13:1 |
| Residence Time, Seconds, | 60 |

EXAMPLE II

In accordance with this example, substantially pure isobutylene was contacted with concentrated HF acid in a stirred autoclave in a heated bath. When the desired quantity of ASO was generated in the ASO reactor, the ASO was added to the acid phase in the reaction zone. The operating conditions and results of the ASO production run are illustrated in Table 2 below:

TABLE 2

| | | |
|---|---|---|
| HF Addition, lbs., | | 1.76 |
| Olefin Addition, lbs., | | 1.18 |
| Composition: | | |
| Propane, Vol. % | — | |
| Propylene, Vol. % | — | |
| Isobutylene, Vol. % | 100 | |
| Normal Butylenes, Vol. % | — | |
| Normal Butane, Vol. % | — | |
| Isobutane, Vol. % | — | |
| ASO in HF, lbs., | | 0.23 |
| Wt. % HF, | 78.0 | |
| Wt % ASO | 13.0 | |
| Mol Wt., Range of ASO, | | 200 to 400 (Estimated) |
| | Specific | |
| Wt. % HF, | 78.0 | |
| Wt. % H$_2$O, | 0.5 | |
| Wt. % ASO, | 13.0 | |
| Wt. % Light H/C | 8.5 (by difference) | |
| ASO Reactor Conditions | Actual | |
| | Specific | |
| Temp., °F., | 106 (avg) | Min = 60° F. Max = 114° F. |
| Pressure, psia, | 183 | |
| Reaction time, min. | 38 | |
| HF/olefin Wt. Ratio | 1.5 | |
| System HF Catalyst, Actual, for HF Alkylation | | |

When operating in accordance with the embodiment of Example II, the ASO reactor should be fed with an HF/olefin weight ratio between about 0.5 and about 5.0, at a temperature of about 50° to about 170° F., preferably about 140° to 160° F. and a pressure of about 50 to about 200 psia (liquid phase) and for a reaction time of about 5 to about 60 minutes. The olefin feed to the ASO reactor is desirably substantially pure isobutylene with preferably not more than 1 to 2% by volume of isobutane based on total olefins. However, the feed can contain up to 25% isobutane based on total olefins without adversely affecting the production of ASO, but a alkylate produced by adding ASO from such feeds to the separated recycle catalyst will be of lower quality (lower octane).

Preferably higher temperatures (140° to 160° F. preferred) are used to decrease the time in the polymerization reaction zone.

While specific examples have been given herein, and specific materials, conditions of operation and equipment are referred to herein, such specific references are by way of example only and are not to be considered limiting.

What is claimed is:

1. A continuous process for alkylating an alkylatable hydrocarbon with a hydrocarbon alkylating agent, comprising:
   (a) reacting said alkylatable hydrocarbon with said hydrocarbon alkylating agent, in the presence of an acid-type catalyst and under alkylation reaction conditions, in an alkylation reaction;
   (b) separating the thus produced effluent from said alkylation reaction into an alkylate product phase and a catalyst phase containing acid-type catalyst and acid-soluble oil produced in said alkylation reaction, in a separation step;
   (c) cooling said catalyst phase, in a cooling step;
   (d) recycling said catalyst phase to said alkylation reaction, in a catalyst recycle step;
   (e) at least intervally withdrawing a portion of said catalyst phase, during said catalyst recycle step and separating the thus withdrawn catalyst phase to obtain a rerun catalyst phase comprising predominantly acid-type catalyst, in a catalyst recovery step; and
   (f) increasing the concentration of acid-soluble oil in said recycle catalyst phase by at least intervally (1)

heating a hydrocarbon alkylating agent to a temperature above the temperature of the thus separated recycle catalyst phase, in a heating step, and (2) reacting the thus heated hydrocarbon alkylating agent with the acid-type catalyst contained in said recycle catalyst phase by adding said heated hydrocarbon alkylating agent to said recycle catalyst phase during said catalyst recycle step but prior to said cooling of said recycle catalyst phase, reacting said heated hydrocarbon alkylating agent with at least a portion of said rerun catalyst phase and adding the reaction product of said heated hydrocarbon alkylating agent and said rerun catalyst phase to said recycle catalyst phase during said catalyst recycle step, reacting said heated hydrocarbon alkylating agent with a fresh acid-type catalyst and adding the reaction product of said heated hydrocarbon alkylating agent and said fresh acid-type catalyst to said recycle catalyst phase during said catalyst recycle step, or any combination of reacting said heated hydrocarbon alkylating agent with said acid-type catalyst in said recycle catalyst phase by adding said heated hydrocarbon alkylating agent to said recycle catalyst phase during said catalyst recycle step but prior to said cooling of said recycle catalyst phase, reacting said heated hydrocarbon alkylating agent with at least a portion of said rerun catalyst phase and adding said reaction product of said heated hydrocarbon alkylating agent and said rerun catalyst phase to said recycle catalyst phase during said catalyst recycle step and reacting said heated hydrocarbon alkylating agent with said fresh acid-type catalyst and adding said reaction product of said heated hydrocarbon alkylating agent and said fresh acid-type catalyst to said recycle catalyst phase during said catalyst recycle step, in an acid-soluble oil production step.

2. A method in accordance with claim 1 wherein the concentration of acid-soluble oil in the recycle catalyst phase is increased by at least intervally heating a hydrocarbon alkylating agent to a temperature above the temperature of the thus separated recycle catalyst phase, in a heating step, and reacting the thus heated hydrocarbon alkylating agent with the acid-type catalyst in said recycle catalyst phase by adding said heated hydrocarbon alkylating agent to said recycle catalyst phase during the catalyst recycle step but prior to the cooling of said recycle catalyst phase, in the acid-soluble oil production step.

3. A process in accordance with claim 1 wherein the concentration of acid-soluble oil in the recycle catalyst phase is increased by at least intervally heating a hydrocarbon alkylating agent to a temperature above the temperature of the thus separated recycle catalyst phase, in a heating step, and reacting the thus heated hydrocarbon alkylating agent with at least a portion of the rerun catalyst phase and adding the reaction product of said heated hydrocarbon alkylating agent and said rerun catalyst phase to said recycle catalyst phase during the catalyst recycle step, in the acid-soluble oil production step.

4. A process in accordance with claim 1 wherein the concentration of acid-soluble oil in the recycle catalyst phase is increased by at least intervally heating a hydrocarbon alkylating agent to a temperature above the temperature of the thus separated recycle catalyst phase, in a heating step, reacting the thus heated hydrocarbon alkylating agent with a fresh acid-type catalyst and adding the reaction product of said heated hydrocarbon alkylating agent and said fresh acid-type catalyst to said recycle catalyst phase during the catalyst recycle step, in the acid-soluble oil production step.

5. A process in accordance with claim 1 wherein the hydrocarbon alkylating agent is at least one $C_4$ olefinic hydrocarbon and the alkylatable hydrocarbon is an isoparaffinic hydrocarbon.

6. A process in accordance with claim 5 wherein the at least one $C_4$ olefinic hydrocarbon is a material selected from the group consisting of isobutylene, butene-1, butene-2's, mixtures of the same and mixtures of the previously mentioned mateials with minor amounts of other hydrocarbons and the alkylatable hydrocarbon is isobutane.

7. A process in accordance with claim 1 wherein the hydrocarbon alkylating agent is a mixture of butenes produced in a catalytic cracking operation.

8. A process in accordance with claim 1 wherein the catalyst is hydrofluoric acid.

9. A process in accordance with claim 1 wherein the hydrocarbon alkylating agent utilized to increase the concentration of acid-soluble oil in the recycle catalyst phase is heated to a temperature between about 160° and about 180° F.

10. A process in accordance with claim 1 wherein the concentration of acid-soluble oil in the recycle catalyst phase is increased to between about 4 and about 25 weight percent of said recycle catalyst phase and is maintained at said concentration of between about 4 and about 25 weight percent of said recycle catalyst phase.

11. A process in accordance with claim 1 which includes at least intervally determining the concentration of acid-soluble oil in the recycle catalyst phase during the catalyst recycle step and the concentration of acid soluble oil in the recycle catalyst phase is increased, as necessary, to maintain a predetermined concentration of acid-soluble oil in the recycle catalyst phase.

12. A process in accordance with claim 1 wherein the hydrocarbon alkylating agent utilized to increase the concentration of acid-soluble oil in the recycle catalyst phase is the same hydrocarbon alkylating agent utilized in the alkylation reaction.

13. A method for starting up a process for alkylating an alkylatable hydrocarbon with a hydrocarbon alkylating agent, in which said hydrocarbon alkylating agent and said alkylatable hydrocarbon are reacted in the presence of an acid-type catalyst and under alkylation reaction conditions, in an alkylation reaction step, the thus produced effluent from said alkylation reaction step is separated into an alkylate product phase and a catalyst phase containing acid-type catalyst and acid-soluble oil produced in said alkylation reaction, in a separation step, the thus separated catalyst phase is cooled, in a cooling step, and the thus cooled catalyst phase is recycled to said alkylation reaction step, in a catalyst recycle step, comprising:

(a) circulating said acid-type catalyst through said alkylation reaction step under said alkylation reaction conditions, through said separation step, through said cooling step and through said catalyst recycle step to establish cyclically circulating catalyst phase; and (b) producing acid soluble oil in said cyclically circulating catalyst phase by heating a hydrocarbon alkylating agent to a temperature above the temperature of said cyclically circulating catalyst phase from said separation step and reacting the thus heated hydrocarbon alkylating agent with said acid-type catalyst in said cyclically circulating catalyst phase by adding the said heated hydrocarbon alkylating agent to said cyclically circulating catalyst phase between said separation step and said cooling step, in an acid-soluble oil production step.

14. A method in accordance with claim 13 wherein the concentration of acid-soluble oil in the cyclically circulating catalyst phase is at least intervally measured and the acid-soluble oil production step is continued until a predetermined concentration of said acid-soluble oil in said cyclically circulating catalyst phase is attained.

15. A method in accordance with claim 14 wherein the reaction of alkylatable hydrocarbon and the hydrocarbon alkylating agent is initiated in the alkylation reaction step, after the predetermined concentration of acid-soluble oil in the cyclically circulating catalyst phase has been attained, the concentration of said acid-soluble oil in said cyclically circulating catalyst phase is at least intervally measured, after said alkylation reaction step is thus initiated and the concentration of acid-soluble oil in said cyclically circulating catalyst phase is increased, as necessary, in the acid-soluble oil production step, to maintain said predetermined concentration of said acid-soluble oil in said cyclically circulating catalyst phase.

16. A method for starting up and operating a process for alkylating an alkylatable hydrocarbon with a hydrocarbon alkylating agent, in which the alkylatable hydrocarbon is alkylated with the hydrocarbon alkylating agent by reacting said alkylatable hydrocarbon with said alkylating agent in the presence of an acid-type catalyst and under alkylation reaction conditions, in an alkylation reaction step, the thus produced effluent from said alkylation step is separated into an alkylate product phase and a catalyst phase containing acid-type catalyst and acid-soluble oil produced in said alkylation reaction step, in a separation step, the thus separated catalyst phase is cooled, in a cooling step, the thus cooled catalyst phase is recycled to said alkylation reaction step, in a catalyst recycle step, and a portion of said catalyst phase is at least intervally withdrawn during said catalyst recycle step and the thus withdrawn catalyst phase is separated to obtain a rerun catalyst phase comprising predominantly acid-type catalyst, in a catalyst recovery step, comprising:
(a) circulating said acid-type catalyst through said alkylation reaction step, under said alkylation reaction conditions, through said separation step, through said cooling step and through said catalyst recycle step to establish a cyclically circulating catalyst phase;
(b) producing acid-soluble oil in said cyclically circulating catalyst phase by heating a hydrocarbon alkylating agent to a temperature above the temperature of said cyclically circulating catalyst phase from said separation step and reacting the thus heated hydrocarbon alkylating agent with said acid-type catalyst in said cyclically circulating catalyst phase by adding said heated hydrocarbon alkylating agent to said cyclically circulating catalyst phase between said separation step and said cooling step, in an acid-soluble oil production step, until a predetermined concentration of acid-soluble oil is present in said cyclically circulating catalyst phase;
(c) initiating said alkylation reaction step by introducing said alkylatable hydrocarbon and said hydrocarbon alkylating agent to said alkylation reaction step; and
(d) at least intervally making up any deficiencies between the concentration of said acid-soluble oil in said cyclically circulating catalyst phase and said predetermined concentration of said acid-soluble oil in said cyclically circulating catalyst phase by heating a hydrocarbon alkylating agent to a temperature above said temperature of said separated cyclically circulating catalyst phase, in a heating step, reacting the thus heated hydrocarbon alkylating agent with the acid-type catalyst in the cyclically circulating catalyst phase by adding said heated hydrocarbon alkylating agent to said cyclically circulating catalyst phase between said separating step and said cooling step, reacting said heated hydrocarbon alkylating agent with at least a portion of said rerun catalyst phase and adding the reaction product of said heated hydrocarbon alkylating agent and said rerun catalyst phase to said cyclically circulating catalyst phase, reacting said heated hydrocarbon alkylating agent with fresh acid-type catalyst and adding a reaction product of said heated hydrocarbon alkylating agent and said fresh acid-type catalyst to said cyclically circulating catalyst phase or any combination of reacting said heated hydrocarbon alkylating agent with said acid-type catalyst in said cyclically circulating catalyst phase by adding said heated hydrocarbon alkylating agent to said cyclically circulating catalyst phase between said separating step and said cooling step, reacting said heated hydrocarbon alkylating agent with at least a portion of said rerun catalyst phase and adding said reaction product of said heated hydrocarbon alkylating agent and said rerun catalyst phase to said cyclically circulating catalyst phase and reacting said heated hydrocarbon alkylating agent with said fresh acid-type catalyst and adding said reaction product of said heated hydrocarbon alkylating agent and said fresh acid-type catalyst to said cyclically circulating catalyst phase.

17. A method in accordance with claim 16 wherein the alkylatable hydrocarbon is an isoparaffinic hydrocarbon and the hydrocarbon alkylating agent is at least one $C_4$ olefinic hydrocarbon.

18. A method in accordance with claim 17 wherein the at least one $C_4$ olefinic hydrocarbon is a material selected from the group consisting of isobutylene, butene-1, butene-2's, mixtures of the same, and mixtures of the previously mentioned materials with minor amounts of other hydrocarbons and the alkylatable hydrocarbon is isobutane.

19. A method in accordance with claim 16 wherein the hydrocarbon alkylating agent is a mixture of butenes produced in a catalytic cracking process.

20. A method in accordance with claim 16 wherein the hydrocarbon alkylating agent utilized to produce the acid-soluble oil is heated to a temperature between about 160° and about 180° F.

21. A method in accordance with claim 16 wherein the acid-type catalyst is hydrofluoric acid.

22. A method in accordance with claim 16 wherein the predetermined concentration of acid-soluble oil in the cyclically circulating catalyst phase is between about 4 and about 25 weight percent of the cyclically circulating catalyst phase.

23. A method in accordance with claim 16 wherein the hydrocarbon alkylating agent utilized to produce acid-soluble oil is the same as the hydrocarbon alkylating agent utilized in the alkylation reaction step.

24. A method in accordance with claim 16 wherein the alkylatable hydrocarbon utilized in the alkylation reaction step is circulated through the alkylation reaction step, the separation step, the cooling step and the catalyst recycle step to establish a cyclically circulating alkylatable hydrocarbon phase prior to the establishment of the cyclically circulating catalyst phase.

25. A method in accordance with claim 16 wherein the alkylating agent utilized in the alkylation reaction step is mixed with the alkylatable hydrocarbon utilized in said alkylation reaction step and said mixture is circulated through the alkylation reaction step, the separation step, the cooling step and the catalyst recycle step to establish a cyclically circulating mixture of saidd alkylatable hydrocarbon and said hydrocarbon alkylating agent prior to the establishment of the cyclically circulating catalyst phase.

* * * * *